United States Patent
Beilfuss et al.

(10) Patent No.: US 9,907,737 B2
(45) Date of Patent: Mar. 6, 2018

(54) COMPOSITION COMPRISING FERULIC ACID ETHYL ESTER AND ARYL ALKANOL

(71) Applicant: L'AIR LIQUIDE, SOCIETE ANONYME POUR L'ETUDE ET L'EXPLOITATION DES PROCEDES GEORGES CLAUDE, Paris (FR)

(72) Inventors: Wolfgang Beilfuss, Hamburg (DE); Klaus Weber, Hamburg (DE); Peter Oltmanns, Hamburg (DE); Sabine Herweg, Norderstedt (DE); Sarah Erichsen, Bad Oldesloe (DE); Carsten Bungenstock, Hamburg (DE); Sonja Luthje, Hamburg (DE)

(73) Assignee: L'AIR LIQUIDE, SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 0 days.

(21) Appl. No.: 15/105,827

(22) PCT Filed: Jul. 4, 2014

(86) PCT No.: PCT/EP2014/064364
§ 371 (c)(1),
(2) Date: Jun. 17, 2016

(87) PCT Pub. No.: WO2015/090634
PCT Pub. Date: Jun. 25, 2015

(65) Prior Publication Data
US 2016/0310382 A1  Oct. 27, 2016

(30) Foreign Application Priority Data
Dec. 18, 2013  (DE) .......................... 10 2013 226 507

(51) Int. Cl.
| | |
|---|---|
| A61K 31/22 | (2006.01) |
| A61K 31/045 | (2006.01) |
| A61K 8/37 | (2006.01) |
| A01N 37/38 | (2006.01) |
| A61K 47/08 | (2006.01) |
| A61K 47/10 | (2017.01) |
| A61K 47/14 | (2017.01) |
| A61K 8/34 | (2006.01) |
| A61Q 19/00 | (2006.01) |
| A61Q 19/08 | (2006.01) |
| A61K 8/06 | (2006.01) |

(52) U.S. Cl.
CPC .............. *A61K 8/37* (2013.01); *A01N 37/38* (2013.01); *A61K 8/062* (2013.01); *A61K 8/34* (2013.01); *A61K 47/08* (2013.01); *A61K 47/10* (2013.01); *A61K 47/14* (2013.01); *A61Q 19/00* (2013.01); *A61Q 19/08* (2013.01); *A61K 2800/10* (2013.01); *A61K 2800/524* (2013.01)

(58) Field of Classification Search
CPC ......... A61K 31/23; A61K 31/06; A61K 31/05
USPC ........................................ 514/549, 728, 730
See application file for complete search history.

(56) References Cited

U.S. PATENT DOCUMENTS

| | | |
|---|---|---|
| 6,114,424 A | 9/2000 | Lahanas et al. |
| 2011/0263646 A1 | 10/2011 | Tarrago et al. |
| 2013/0142740 A1* | 6/2013 | Cziryak ................. A01N 37/10 424/60 |
| 2014/0179645 A1 | 6/2014 | Arndt |

FOREIGN PATENT DOCUMENTS

| | | |
|---|---|---|
| CA | 2012288 A1 | 9/1990 |
| DE | 10 2012 212 281 B3 | 10/2013 |
| EP | 2 022 489 A1 | 2/2009 |
| FR | 2 921 560 A1 | 4/2009 |
| WO | 2013/080140 A2 | 6/2013 |
| WO | 2013/091775 A2 | 6/2013 |

OTHER PUBLICATIONS

Markham, K., et al., "HPLC and GC-MS Identification of the Major Organic Constituents in New Zealand Propolis," Phytochemistry, vol. 42, No. 1, May 1996, pp. 205-211.
Tava, A., et al., "Volatile Compounds from Leaves and Flowers of Bituminaria Bituminosa (L.) Stirt. (Fabaceae) from Italy," Flavour and Fragrance Journal, vol. 22, No. 5, 2007, pp. 363-370.
Radulovic, N., et al., "GC-MS Analyses of Flower Ether Extracts of Prunus Domestica L. and Prunus Padus L. (Rosaceae)," Chemical Papers, vol. 63, No. 4, Aug. 2009, pp. 377-384.
Khatkar, A., et al., "Synthesis and Anitmicrobial Evaluation of Ferulic Acid Derivatives," Research on Chemical Intermediates, Chemical Abstracts Service, 2013, 1 page.
Khatkar, A., et al., "Synthesis and Anitmicrobial Evaluation of Ferulic Acid Derivatives," Research on Chemical Intermediates, Apr. 2013, 11 pages.
Komatsu, et al., "Studies on the Characterization of White Wine from Koshu Grape Viticulture (3rd Report)," , Chemical Abstracts Service, 2009, 1 page.
"Chapter 2: P-Hydroxycinnamic Acid Conjugates as Multiactive Agents for Cosmetics and Dermatics," pp. 17-65 with English Translation.
Eggensperger, H., et al., "On the Multi-Active Effect of Ferulic Acid and its Esters in Cosmetics," Part II—Continuation from SOFW-Journal, vol. 122, No. 3, 1996, pp. 210-215, with English Translation.
Eggensperger, H., et al., "On the Multi-Active Effect of Ferulic Acid and its Esters in Cosmetics," Part I-SOFW-Journal, vol. 122, No. 3, 1996, pp. 146-157, with English Translation.
Mineral Moisturized Eye Cream 30 ml from the Dead Sea, Eye Creams, Jan. 30, 2013, 11 pages, http://archiwum.allegro.pl/oferta/mineralium-krem-pod-poj-30ml-z-morza-martwego-i2954635569.html.

(Continued)

*Primary Examiner* — Raymond Henley, III
(74) *Attorney, Agent, or Firm* — Young & Thompson

(57) ABSTRACT

A composition which includes a) ferulic acid ethyl ester and b) one, two or more aryl alkanols. The combination of components a) and b) has an antimicrobial effect on products such as cosmetics.

15 Claims, No Drawings

(56) References Cited

OTHER PUBLICATIONS

AnneMarie Borlind, Natural Beaty, Sun DNA Protect LSF 30, 50ml, Ecoinform, List of Ingredients, 2013, 4 pages.

Michiyo, N., et al., "Antimicrobial Activities of Synthetic Ferulic Acid Derivatives," Food Preservation Science, vol. 28, No. 4, 2002, pp. 183-188 —with English translation.

Codechek: Olivenol Intensive Light Cream, 50ml, Facial Cream for Normal to Dry Skin, 2014, 9 pages http://www.codecheck.info/kosmetik_koerperpflege/gesichtspflege/gesichtscremen/ean_4016369403358/id_13595810/OLIVENOEL_Intensivcreme_leicht_50_Milliliter.pro—with English Translation.

Merkl, R., et al., "Antimicrobial and Antioxidant Properties of Phenolic Acids Alkyl Esters," Czech J. Food Sci., vol. 28, No. 4, 2010, pp. 275-279.

International Search Report issued in Application No. PCT/EP2014/064364, dated Oct. 14, 2014.

* cited by examiner

COMPOSITION COMPRISING FERULIC ACID ETHYL ESTER AND ARYL ALKANOL

The present invention relates to a composition which comprises a) ferulic acid ethyl ester and b) one, two or more aryl alkanols. The composition can be for example in the form of an (antimicrobial acting) concentrate or an (antimicrobial containing) consumer product (for example a cosmetic). Furthermore, the invention relates to the use of the concentrate for providing the antimicrobial effect in topically applied consumer products. The invention also relates to the use of ferulic acid ethyl ester to improve the antimicrobial effect of a consumer product which comprises one, two or more aryl alkanols.

For the preservation of cosmetics usually active ingredients such as formaldehyde separators, p-hydroxybenzoic acid esters (parabens), organic acids, isothiazolin-3-one, aromatic alcohols such as phenoxy ethanol or benzyl alcohol, combinations with phenethyl alcohol and combinations with phenyl propanol are used. The disadvantage of some of these active ingredients is their low stability and significant odour. Furthermore, the number of usable active ingredients is becoming more and more restricted by toxicological and regulatory requirements. In the cosmetics market active ingredients are increasingly required for preservation which are as far possible gentle on the skin and of natural origin.

CA 2,012,288 A relates to the use of a combination of a) a phenolic compound, b) aromatic alcohol and c) wetting agents, surfactants and the usual additives as disinfectants for plant hygiene. Ferulic acid is described as a phenolic compound (i.e. 4-hydroxy-3-methoxy cinnamic acid).

The particularly preferred aromatic alcohol is phenoxy ethanol.

H. Eggensperger (Multiaktive Wirkstoffe in Kosmetika, Verlag für Chemische Industrie 2000, volume 2, p. 19-65) describes an antioxidant effect, a light protection effect, a deodorant effect, an anti-inflammatory effect and an antimicrobial effect for ferulic acid. For ferulic acid ethyl ester a cosmetic effect is described (cf. also H. Eggensperger and M. Wilker, SÖFW-Journal, 122. Jg., March 1996, p. 146-156; April 1996, p. 210-215 and August 1996, p. 554-556).

For the product CELLIGENT® of the company Rahn A G, Zürich, Switzerland with a content of ferulic acid ethyl ester, said ester is a natural antioxidant with UV-absorbing properties. FR 2 921 560 A1 describes ferulic acid as part of a preservative composition. Apart from the fact that ferulic acid ethyl ester is an expensive active ingredient, it also has poor water solubility and would thus not be suitable as the only solid matter used for the antimicrobial function, in particular for the aqueous phase of cosmetic or pharmaceutical emulsions. During preliminary work on the present invention it was also discovered that ferulic acid ethyl ester has a much weaker antimicrobial effect than ferulic acid itself. It is known to persons skilled in the art that carboxylic acid esters are typically much less effective anti-microbially than the underlying carboxylic acids. A disadvantage of carboxylic acids as antimicrobial agents is however that they are normally only effective in the acidic pH-range and their applicability in cosmetics is thus restricted.

WO 2013/080140 A2 describes a preservation system for sunscreens which comprises a combination of UV-filters, aromatic carboxylic acid or salt thereof, aromatic alcohol and cosmetically acceptable aqueous carriers. An example of an aromatic carboxylic acid is ferulic acid. Alternatively, esters of anisic acid are described as derivatives of an aromatic carboxylic acid. The preferred aromatic alcohol is phenoxy ethanol.

WO 2013/091775 A2 discloses the use of selected cyclohexanol derivatives as antimicrobial active ingredients for cosmetic preparations. The preparations can be combined for controlling pigmentation for example with ferulic acid or be made antimicrobial by ferulic acid.

Furthermore, aromatic alcohols such as phenoxy ethanol (an aryloxy alkanol) are used for the antimicrobial activity in cosmetics (cf. also DE 10 2012 212 281 B3). However, phenoxy ethanol is currently under discussion and may be reduced or banned for some applications, e.g. for baby products. In general, aryloxy alkanols are becoming less acceptable to consumers worldwide.

The underlying objective of the present invention is thus to provide combinations of active ingredients for antimicrobial purposes (i.e. preservation) of cosmetics. This combination of active ingredients should be based on active ingredients, which when used do not exhibit the described disadvantages of known active ingredients and combinations of active ingredients. The combinations of active ingredients should be based on natural or nature-identical components and be effective in a concentration that is as low as possible. In addition, they should also be versatile, i.e. their use should not be restricted to a specific pH value of the product to be preserved.

It has been found surprisingly that this objective is achieved by a composition which comprises:
  a) ferulic acid ethyl ester and
  b) one, two or more aryl alkanols.

The invention is also based on the fact that it has been found that combinations of a) ferulic acid ethyl ester with b) one, two or more aryl alkanols act synergistically, wherein the ferulic acid ethyl ester only having an antimicrobial effect in comparatively high concentrations increases the effect of aryl alkanols even in very low concentrations (i.e. acts as a booster).

It has also been shown that 3-phenyl-1-propanol (an aryl alkanol) although not previously listed as a preservative, has a good anti-microbial effect and is nature-identical. However, all aryl alkanols have a clear characteristic odour, which is in part more intensive than the characteristic odour of aryloxy alkanols. Although by means of the improved anti-microbial effect of the aryl alkanols with the use of a) ferulic acid ethyl ester (this effect is much more pronounced than with aryloxy alkanols) the required amount of aryl alkanol required for preservation can be reduced.

The teaching of the invention thus permits the natural or nature-identical preservation or antimicrobial stabilisation of leave-on formulations for cosmetics, i.e. the provision of antimicrobial products as preservative-free cosmetics.

a) Ferulic Acid Ethyl Ester

As the ferulic acid ethyl ester cis-ferulic acid ethyl ester, trans-ferulic acid ethyl ester and cis/trans-mixtures of natural and synthetic origin are suitable. Preferably, component a) is the trans-form of ferulic acid ethyl ester.

b) Aryl Alkanol

In a preferred embodiment the aryl alkanol is selected from 3-phenyl-1-propanol, phenethyl alcohol, veratryl alcohol, benzyl alcohol, 4-methyl-benzyl alcohol and 2-methyl-1-phenyl-2-propanol, preferably 3-phenyl-1-propanol, phenethyl alcohol and benzyl alcohol. In particular, component b) is 3-phenyl-1-propanol or a mixture of 3-phenyl-1-propanol with benzyl alcohol. In particular, it is preferred that component b) is 3-phenyl-1-propanol (as the only aryl alkanol).

Concentrate

According to a first alternative the composition is in the form of a concentrate and comprises:

a) From 1 wt. % to 30 wt. %, preferably 8 wt. % to 20 wt. %, in particular 10 wt. % to 18 wt. %, such as 12 wt. % to 16 wt. %, for example about 14 wt. % ferulic acid ethyl ester and b) From 70 wt. % to 95 wt. %, preferably 80 wt. % to 92 wt. %, in particular 82 wt. % to 90 wt. %, such as 84 wt. % to 88 wt. %, for example about 86 wt. % of the one, two or more aryl alkanols.

According a particular embodiment, the composition as hereinbefore defined, comprises:

a) From 8 wt. % to 20 wt. %, ferulic acid ethyl ester and b) From 80 wt. % to 92 wt. %, in particular 82 wt. % to 90 wt. %, such as 84 wt % to 88 wt. %, for example about 86 wt. % of the one, two or more aryl alkanols.

A particularly preferred concentrate comprises:

a) 10 wt. % to 18 wt. %, such as 12 wt. % to 16 wt. %, for example about 14 wt. % ferulic acid ethyl ester and b) 82 wt. % to 90 wt. %, such as 84 wt. % to 88 wt. %, for example about 86 wt. % 3-phenyl-1-propanol.

If the composition is in the form of a (typically liquid) concentrate, it can comprise c) further active ingredients or additives, such as 1,3-propanediol, vanillyl butyl ether, 1-(2-ethyl hexyl) glycerine ether (commercial product Sensiva® SC 50 of the company Schülke & Mayr GmbH, Norderstedt, Germany, which is stabilised with Vitamin E), 1,2-octanediol, 1-undecanol, 1,2-pentanediol or ferulic acid, or mixtures thereof.

Particularly preferably, the concentrate according to the invention contains no other components apart from a) ferulic acid ethyl ester and b) the one, two or more aryl alkanols (preferably 3-phenyl-1-propanol alone), that is the concentrate preferably consists of the components a) ferulic acid ethyl ester and b) the one, two or more aryl alkanols. In particular, a concentrate is preferred which consists of a) ferulic acid ethyl ester and b) 3-phenyl-1-propanol, i.e. which contains no other components apart from these two components.

Consumer Product

According to a second alternative, the composition is provided as a consumer product, wherein the consumer product is preferably a topically applied consumer product (i.e. externally, locally), in particular a topically applied leave-on consumer product, such as for example a topically applied o/w or w/o consumer product, for example an o/w or a w/o lotion or an o/w or a w/o emulsion.

The consumer product is preferably a cosmetics product, a dermatological mixture, a pharmaceutical mixture or a technical product, preferably a cosmetics product.

Typically an antimicrobially effective consumer product according to the invention comprises:

a) From 0.01 to 1.0 wt. %, preferably 0.02 to 0.5 wt. %, in particular 0.04 to 0.25 wt. %, such as 0.06 to 0.15 wt. %, for example about 0.1 wt. % ferulic acid ethyl ester and b) 0.1 to 4 wt. %, preferably 0.2 to 2 wt. %, in particular 0.3 to 1.0 wt. %, such as 0.4 to 0.8 wt. %, for example about 0.6 wt. % of the one, two or more aryl alkanols, wherein component b) is particularly preferably specifically 3-phenyl-1-propanol.

According to a particular embodiment the consumer product as hereinbefore defined, is a cosmetic preparation which comprises for 100% by weight, one or more topically acceptable ingredients, from 0.02 wt. % to 0.5 wt. % ferulic acid ethyl ester and from 0.2 wt. % to 2 wt. %, of one, two or more aryl alkanols.

The invention also relates to the use of the concentrate for providing an antimicrobial effect in topically applied consumer products, in particular for the antimicrobial preservation of topically applied leave-on consumer products, for example for the antimicrobial preservation of topically applied o/w consumer products, such as cosmetic creams or emulsions.

In addition, the invention relates to the use of ferulic acid ethyl ester to improve the antimicrobial preservation of a consumer product, which comprises one, two or more aryl alkanols. In other words, a) ferulic acid ethyl ester and b) aryl alkanol act synergistically with respect to the antimicrobial effect of cosmetics, i.e. the effect clearly exceeds what would have been expected from the effects of the individual components.

The invention thus provides the following advantages:
  reduction in the concentration of aryl alkanol,
  low concentration compared to conventional "natural preservatives",
  improved market acceptance,
  improved protection of the skin from free radicals,
  improved anti-aging properties,
  good fungicidal effect in comparatively low concentrations,
  use of a nature-identical, preservative-free active ingredient system for antimicrobial stabilisation,
  anti-inflammatory effect and
  pH-independent activity.

Advantages of 3-phenyl-1-propanol:
  pH-neutral,
  pH-independent effect, i.e. also effective in (weak) alkaline cosmetics.

Advantages of ferulic acid ethyl ester:
  protects the skin from free radicals,
  soothing to skin, anti-inflammatory, anti-aging properties.

The advantages of the invention are described in particular in the following examples. The percentages relate to weight, unless otherwise indicated.

EXAMPLES

Method 1: Bacterial Count Reduction Test

The aim of this bacterial count reduction test is to determine suitable preservatives and reaction times for samples injected in the laboratory.

Solutions and Culture Media Used:
CSA Casein peptone-Soy flour peptone-Agar
SA Sabouraud-Agar
CSL Casein peptone-Soy flour peptone-Boullion
NaCl physiological sodium chloride solution, 0.85%

Test Organisms Used

*Staphylococcus aureus, Escherichia coli* or *Pseudomonas aeruginosa, Candida albicans, Aspergillus brasiliensis*

Preparation of the Injection Solution

Bacteria:

From a 24-hour CS-angular agar culture (I subculture) of *Staphylococcus aureus/Escherichia coli* 24-hour CSL-cultures (II subculture) are created. The incubation is carried out at 37° C. The titer of the bacterial suspension is about $10^9$ CFU/ml.

Yeast:

A 4 day old *Candida albicans* culture on SA-agar (II subculture) is washed with 5 ml physiological NaCl and adjusted according to a barium sulphate standard (cf. DVG Guidelines). The titer of the *Candida albicans* suspension is $10^8$ CFU/ml.

Moulds:

A 7 to 14 days old *Aspergillus brasiliensis* culture on SA agar (25° C.±1° C.) is washed with 5 ml physiological NaCl, filtered by a glass funnel with glass wool and filled with physiological NaCl to 100 ml. The titre of the *Aspergillus brasiliensis* suspension is about $10^7$ CFU/ml.

The titres of the respectively produced test organism suspensions are determined by means of a dilution series in physiological NaCl and recorded.

Implementation:

The samples are displaced with different concentrations of suitable preservatives. For each test bacterium a dilution series is required. The samples are injected individually with the respective test organism suspension and stirred well:

25 g samples=0.1 ml bacterial suspension
50 g samples=0.2 ml bacterial suspension After the indicated reaction times the samples are firstly stirred homogenously with a sterile glass rod and then spread onto CSA or SA agar. The bacteria samples are spread onto CSA and incubated for 48 hours at 37° C. The mould and yeast samples are spread onto SA agar and incubated for 48 hours at 37° C. (*Candida albicans*) and at 25° C. (*Aspergillus brasiliensis*).

Method 2: KoKo Test

The test described in the following is performed to determine the preservative effect in cosmetic formulations.

Principle

By means of the described method the effectiveness of chemical preservatives is to be tested with respect to the in-can preservation of cosmetic formulations. For this in various different trials the preservatives to be tested are added in different concentrations to unpreserved samples. A continuous bacterial load is achieved by periodically injecting the test media. Parallel to the injection smears are taken of the individual media immediately before this. An assessment is made with regard to the microbial growth of the smears. The longer the period up to the first appearance of microbial growth, the more effective the preservative.

Implementation 25 g of the cosmetic to be tested is weighed out into wide neck bottles with a screw closure (LDPE). The preservatives to be tested are added in separate deposits in their application concentrations. An unpreserved sample is used as a growth control. Two days after the addition of the preservative the samples are infected with 0.1 ml of an injection solution consisting of the following test organisms. The injection solution has a titre of about $10^7$-$10^8$ bacteria/ml (Table 1).

TABLE 1

| Bacteria | Gram-positive | | *Staphylococcus aureus* | ATCC 6538 |
|---|---|---|---|---|
| | | | *Kocuriarhizophila* | ATCC 9341 |
| | Gram-negative | Enterobacteria | *Enterobacter gergoviae* | ATCC 33028 |
| | | | *Escherichia coli* | ATCC 11229 |
| | | | *Klebsiella pneumoniae* | ATCC 4352 |
| | | *Pseudomonas* | *Pseudomonas aeruginosa* | ATCC 9027 |
| | | | *Pseudomonas fluorescens* | ATCC 17397 |
| | | | *Pseudomonas putida* | ATCC 12633 |
| | Yeast | | *Candida albicans* | ATCC 10231 |
| | Moulds | | *Aspergillus brasiliensis* | ATCC 16404 |
| | | | *Penicillium pinophilum* | ATCC 36839 |

The test deposits are then spread once a week onto agar plates (Casein peptone-Soy flour peptone-Agar (CSA) for bacteria and Sabouraud dextrose Agar (SA) for yeasts and moulds) and then injected. The first smear (sterility test) is performed on both uninhibited (TLSH) and non-uninhibited culture media in order to reveal as far as possible all of the initial contamination. The assessment of the microbial growth of the smears is performed after a three-day incubation at 25° C. Negative smears are observed for a further two days as a precaution and then assessed again. The assessment of the preservative effect of the individual product concentrations is performed in a semi-quantitative method over the growth of the individual smears.

| Symbol | Meaning | Germs count/ml |
|---|---|---|
| − | No growth | <100 |
| + | Slight growth | About $10^2$ |
| ++ | Moderate growth | About $10^3$ |
| +++ | Heavy growth | About $10^4$ |
| ++++ | Massive growth | About $10^5$ |
| R | Surface covered | About $10^6$ |
| ./. | Test terminated | |

The growth is differentiated for bacteria (B), yeasts (S) and moulds (H). The experiment is performed for a maximum of six weeks, i.e. over six injection cycles, or terminated (./.) after repeated heavy growth (+++).

Assessment of the Results

The sample is well preserved according to criterion A if under the aforementioned laboratory conditions it survives a period of six weeks without bacteria affecting the samples, i.e. if there is no evidence of microbial growth even after the sixth injection. From many years' experience of this test method it is possible to define a microbiological stability of over 30 months recommended for cosmetics.

If the sample exhibits low microbial growth (+) during the six injection cycles the sample meets criterion B. A B criterion can represent adequate preservation if the microbiological risk analysis comprises control factors independent of the formulation. This could include for example the use of packaging including a pump instead of a can and/or the high demands of good manufacturing practice (GMP).

Example 1

The results of a test performed according to method 1 are shown in Table 2 and show the improved effectiveness of the combination of 0.7% (ferulic acid+3-phenyl-1-propanol) and in particular 0.7% (ferulic acid ethyl ester+3-phenyl-1-propanol) compared to 0.75% 3-phenyl-1-propanol alone. They also show the only moderate effectiveness of the combination of ferulic acid (2-ethyl hexyl) ester+3-phenyl-1-propanol and that the combinations according to the invention are advantageous especially with the ethyl ester of ferulic acid.

However, the 9:1 mixtures of ferulic acid ester with the aryloxy alkanol phenoxy ethanol show hardly any advantages over phenoxy ethanol alone, which shows that the effectiveness of the combinations according to the invention with the aryl alkanol 3-phenyl-1-propanol was surprising. Furthermore, the effectiveness on moulds with a comparatively low concentration of active ingredients is clear.

Example 2

The results of a test performed according to method 2 are shown in Table 3 and prove the effectiveness of the 6:1 combination of 3-phenyl-1-propanol+ferulic acid ethyl ester (at least criterion B) and show the greater effectiveness over a 6:1 mixture of phenoxy ethanol+ferulic acid ethyl ester.

Example 3

The results of a test performed according to method 1 are also shown in Table 4 and prove the inherent effectiveness of the ferulic acid on bacteria, whereas the ferulic acid esters themselves are not effective in a comparatively high concentration of 2%. As a result it was surprising that a combination containing a ferulic acid ester is more effective.

TABLE 2

| Initial bacterial count | *S. aureus* ATCC: 6538<br>$1 \times 10^9$ | | | | *E. coli* ATCC: 11229<br>$1.3 \times 10^9$ | | | |
|---|---|---|---|---|---|---|---|---|
| Hours | 24 | 72 | 168 | 336 | 24 | 72 | 168 | 336 |
| Blank value (o/w cream) | R | R | ++++ | +++ | R | R | R | R |
| 0.9% phenoxy ethanol | R | ++++ | ++++ | +++ | + | — | — | ++++ |
| 0.1% ferulic acid | R | ++++ | ++++ | ++++ | ++++ | R | R | R |
| 0.1% ferulic acid + 0.9% phenoxy ethanol | +++ | +++ | + | + | — | — | — | — |
| 0.1% ferulic acid-2-ethylhexylester | ++++ | ++++ | ++++ | +++ | R | ++++ | R | R |
| 0.1% ferulic acid (2-ethyl hexyl) ester + 0.9% phenoxy ethanol | ++++ | ++++ | +++ | ++ | — | — | — | — |
| 0.1% ferulic acid-ethyl ester | ++++ | R | R | ++++ | R | R | ++++ | R |
| 0.1% ferulic acid ethyl ester + 0.9% phenoxy ethanol | +++ | +++ | +++ | + | — | — | — | — |
| 0.75% 3-phenyl-propanol-1 | ++++ | ++++ | +++ | — | ++ | — | — | — |
| 0.7% 3-phenyl-1-propanol+ ferulic acid (3:1) | ++ | + | — | — | — | — | — | — |
| 1.0% 3-phenyl-1-propanol + ferulic acid (3:1) | — | — | — | — | — | — | — | — |
| 0.7% 3-phenyl-1-propanol + ferulic acid (6:1) | ++++ | + | — | — | — | — | — | — |
| 1.0% 3-phenyl-1-propanol + ferulic acid (6:1) | — | — | — | — | — | — | — | — |
| 0.7% 3-phenyl-1-propanol + ferulic acid-(2-ethyl hexyl) ester (3:1) | ++++ | ++++ | +++ | — | +++ | + | — | — |
| 1.0% 3-phenyl-1-propanol + ferulic acid (2-ethyl hexyl) ester (3:1) | +++ | +++ | ++ | — | — | — | — | — |
| 0.7% 3-phenyl-1-propanol + ferulic acid (2-ethyl hexyl) ester (6:1) | ++++ | +++ | ++ | — | — | — | — | — |
| 1.0% 3-phenyl-1-propanol + ferulic acid (2-ethyl hexyl) ester (6:1) | +++ | ++ | — | — | — | — | — | — |
| 0.7% 3-phenyl-1-propanol + ferulic acid ethyl ester (3:1) | ++++ | +++ | + | — | — | — | — | — |
| 1.0% 3-phenyl-1-propanol + ferulic acid ethyl ester (3:1) | ++ | + | + | — | — | — | — | — |
| 0.7% 3-phenyl-1-propanol + ferulic acid ethyl ester (6:1) | +++ | +++ | + | — | — | — | — | — |
| 1.0% 3-phenyl-1-propanol + ferulic acid ethyl ester (6:1) | ++ | + | — | — | — | — | — | — |

TABLE 2

| Initial bacterial count | *C. albicans* ATCC: 10231<br>$4.1 \times 10^8$ | | | | *A. brasiliensis* ATCC: 16404<br>$1.5 \times 10^7$ | | | |
|---|---|---|---|---|---|---|---|---|
| Hours | 24 | 72 | 168 | 336 | 24 | 72 | 168 | 336 |
| Blank value (o/w cream) | R | R | R | R | R | ++++ | ++++ | ++++ |
| 0.9% phenoxy ethanol | ++++ | R | +++ | — | ++++ | ++++ | ++ | — |
| 0.1% ferulic acid | R | R | ++++ | ++++ | ++++ | ++++ | ++++ | ++++ |
| 0.1% ferulic acid + 0.9% phenoxy ethanol | R | ++++ | ++ | — | +++ | ++ | + | — |
| 0.1% ferulic acid (2-ethyl hexyl) ester | ++++ | ++++ | ++++ | ++++ | R | ++++ | ++++ | ++++ |
| 0.1% ferulic acid (2-ethyl hexyl) ester + 0.9% phenoxy ethanol | ++++ | ++++ | +++ | — | +++ | +++ | ++ | — |
| 0.1% ferulic acid ethyl ester | R | R | R | R | ++++ | ++++ | ++++ | +++ |
| 0.1% ferulic acid ethyl ester + 0.9% phenoxy ethanol | R | +++ | — | — | ++++ | +++ | + | — |
| 0.75% 3-phenyl-1-propanol | ++++ | ++++ | + | — | ++++ | +++ | + | — |
| 0.7% 3-phenyl-1-propanol + ferulic acid (3:1) | ++++ | +++ | — | — | +++ | +++ | + | — |

TABLE 2-continued

| Initial bacterial count | C. albicans ATCC: 10231 4.1 × 10⁸ | | | | A. brasiliensis ATCC: 16404 1.5 × 10⁷ | | | |
|---|---|---|---|---|---|---|---|---|
| 1.0% 3-phenyl-1-propanol + ferulic acid (3:1) | +++ | — | — | — | ++ | ++ | — | — |
| 0.7% 3-phenyl-1-propanol + ferulic acid (6:1) | R | +++ | — | — | +++ | +++ | — | — |
| 1.0% 3-phenyl-1-propanol + ferulic acid (6:1) | ++++ | — | — | — | +++ | ++ | — | — |
| 0.7% 3-phenyl-1-propanol + ferulic acid-2-ethyl-hexylester (3:1) | ++++ | ++++ | +++ | — | ++++ | ++++ | ++ | — |
| 1.0% 3-phenyl-1-propanol + ferulic acid (2-ethyl hexyl) ester (3:1) | ++++ | +++ | — | — | ++++ | +++ | — | — |
| 0.7% 3-phenyl-1-propanol + ferulic acid (2-ethyl hexyl) ester (6:1) | ++++ | +++ | + | — | +++ | +++ | — | — |
| 1.0% 3-phenyl-1-propanol + ferulic acid (2-ethyl hexyl) ester (6:1) | ++++ | +++ | — | — | ++ | ++ | — | — |
| 0.7% 3-phenyl-1-propanol + ferulic acid ethyl ester (3:1) | +++ | + | — | — | +++ | +++ | — | — |
| 1.0% 3-phenyl-1-propanol + ferulic acid ethyl ester (3:1) | +++ | — | — | — | ++ | ++ | — | — |
| 0.7% 3-phenyl-1-propanol + ferulic acid ethyl ester (6:1) | ++++ | +++ | — | — | ++++ | +++ | — | — |
| 1.0% 3-phenyl-1-propanol + ferulic acid ethyl ester (6:1) | +++ | — | — | — | +++ | +++ | — | — |

TABLE 3

| Product | pH | Sterile smear | Injection cycle | | | | | |
|---|---|---|---|---|---|---|---|---|
| | | | 1 | 2 | 3 | 4 | 5 | 6 |
| Blank value (o/w cream) | 7.0 | — | +++ B,S | +++ S,H,B | ./. | | | |
| 0.1% ferulic acid ethyl ester + 0.6% 3-phenyl-1-propanol | 7.0 | — | — | — | — | +B | — | +B |
| 0.1% ferulic acid ethyl ester + 0.6% 3-phenyl-1-propanol | 7.0 | — | ++ S | +++ S | +++ S | ./. | | |

TABLE 4

| Bacteria | S. aureus ATCC: 6538 | | | | P. aeruginosa ATCC: 9027 | | | |
|---|---|---|---|---|---|---|---|---|
| Initial bacterial count | 2.2 × 10⁹ | | | | 1.2 × 10⁹ | | | |
| Hours | 24 | 72 | 168 | 336 | 24 | 72 | 168 | 336 |
| Blank value (o/w-Lotion) | R | R | ++++ | ++++ | ++++ | ++++ | ++++ | +++ |
| 2.0% ferulic acid | — | — | — | — | — | — | — | — |
| 2.0% ferulic acid (2-ethyl hexyl) ester | R | ++++ | ++++ | ++++ | +++ | ++++ | ++++ | ++++ |
| 2.0% ferulic acid ethyl ester | ++++ | ++++ | +++ | +++ | ++++ | ++++ | ++++ | ++++ |

| Bacteria | C. albicans ATCC: 10231 | | | | A. brasiliensis ATCC: 16404 | | | |
|---|---|---|---|---|---|---|---|---|
| Initial bacterial count | 5.4 × 10⁸ | | | | 7.7 × 10⁷ | | | |
| Hours | 24 | 72 | 168 | 336 | 24 | 72 | 168 | 336 |
| Blank value (o/w-Lotion) | R | R | ++++ | ++++ | R | R | R | R |
| 2.0% ferulic acid | R | R | ++++ | ++++ | ++++ | ++++ | ++++ | ++++ |
| 2.0% ferulic acid (2-ethyl hexyl) ester | R | R | ++++ | ++++ | ++++ | ++++ | ++++ | ++++ |
| 2.0% ferulic acid ethyl ester | ++++ | ++++ | +++ | +++ | ++ | +++ | +++ | ++++ |

Example 4

The results of a test carried out according to method 2 are represented below in Table 5 and show the effectiveness (KoKo test passed with A criterion) of the particularly preferred concentrate of a) ferulic acid ethyl ester and b) 3-phenyl-1-propanol in a weight ratio of 1:6

TABLE 5

| pH 5.5 | Sterile smear | Injection cycles | | | | | |
|---|---|---|---|---|---|---|---|
| | | 1 | 2 | 3 | 4 | 5 | 6 |
| Blank value (o/w-Lotion) | — | +++ B,H,S | +++ B,H,S | ./. | | | |
| 1% ferulic acid ethyl ester + 3-phenyl propanol (1:6) | — | — | — | — | — | — | — |

The invention claimed is:

1. A composition comprising:
   a) from 1 wt. % to 30 wt. % of ferulic acid ethyl ester and
   b) from 70 wt. % to 95 wt. % of one, two or more aryl alkanols,
   wherein the composition is a concentrate.

2. The composition according to claim 1, wherein component a) is selected from cis-ferulic acid ethyl ester, trans-ferulic acid ethyl ester and mixtures thereof.

3. The composition according to claim 1, wherein the one, two or more aryl alkanols are selected from the group consisting of 3-phenyl-1-propanol, phenethyl alcohol, veratryl alcohol, 4-methyl-benzyl alcohol, benzyl alcohol and 2-methyl-1-phenyl-2-propanol.

4. The composition according to claim 3, wherein component b) is 3-phenyl-1-propanol or a mixture of 3-phenyl-1-propanol with benzyl alcohol.

5. The composition according to claim 1, further comprising c) 1,3-propanediol, vanillyl butyl ether, 1-(2-ethylhexyl)glycerinether, 1,2-octanediol, 1-undecanol, 1,2-pentanediol, ferulic acid or mixtures thereof.

6. The composition according to claim 1, comprising:
   a) From 10 wt. % to 18 wt. % of ferulic acid ethyl ester and
   b) From 82 wt. % to 90 wt. % of 3-phenyl-1-propanol.

7. A consumer product comprising the composition according to claim 1.

8. The consumer product according to claim 7, wherein the consumer product comprises
   a) 0.01 wt. % to 1.0 wt. % of ferulic acid ethyl ester and
   b) 0.1 wt. % to 4 wt. %, of one, two or more aryl alkanols.

9. The consumer product according to claim 7 wherein the consumer product is present as an o/w or w/o emulsion.

10. A topically applied consumer product, comprising the composition according to claim 1, wherein composition provides an antimicrobial effect.

11. The topically applied consumer product according to claim 10, wherein the topically applied consumer product is a topically applied leave-on consumer product.

12. The topically applied consumer product according to claim 11, wherein the topically applied consumer product is a topically applied o/w or w/o consumer product.

13. The composition according to claim 2, wherein component a) is trans-ferulic acid ethyl ester.

14. The composition according to claim 3, wherein the one, two or more aryl alkanols are 3-phenyl-1-propanol, phenethyl alcohol and benzyl alcohol.

15. The composition according to claim 4, wherein component b) is 3-phenyl-1-propanol.

* * * * *